United States Patent [19]

Bucalo

[11] 3,999,611
[45] Dec. 28, 1976

[54] DEVICES RELATING TO HOOVES

[76] Inventor: Louis Bucalo, 155 Roberts St., Holbrook, N.Y. 11741

[22] Filed: Nov. 18, 1974

[21] Appl. No.: 524,742

[52] U.S. Cl. .................................................. 168/4
[51] Int. Cl.² ...................................... A01K 47/06
[58] Field of Search ............ 168/DIG. 1, 4, 18, 21, 168/22, 24, 17, 14, 20; 128/2 S, 2 N; 272/69, 73

[56] References Cited

UNITED STATES PATENTS

| | | | |
|---|---|---|---|
| 905,690 | 12/1908 | Gimbut | 168/17 |
| 979,365 | 12/1910 | Barclay | 168/14 |
| 1,688,251 | 10/1928 | Trakalo | 168/17 |
| 3,285,346 | 11/1966 | Jenny et al. | 168/DIG. 1 |
| 3,628,608 | 12/1971 | Shermann | 168/14 |

OTHER PUBLICATIONS

"On the Sensitivity Calibration of Implanted Transducers" IEEE Transactions on Bio-Medical Eng., Oct. 1970, Bicker et al.
"Leg Load Warning" Medical and Biological Engineering, Donald Endicott et al., May, 1974.

*Primary Examiner*—Louis G. Mancene
*Assistant Examiner*—Jack Q. Lever
*Attorney, Agent, or Firm*—Steinberg & Blake

[57] ABSTRACT

Devices for obtaining information with respect to the behavior of a hoof. A sensing device such as an accelerometer or load cell may be attached to the hoof to respond to forces such as impact of the hoof on the ground, and the information derived from the sensing device may be recorded.

6 Claims, 15 Drawing Figures

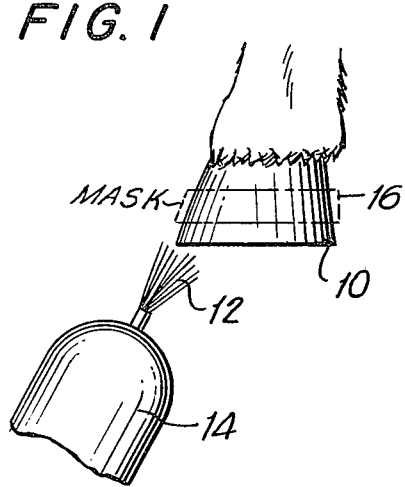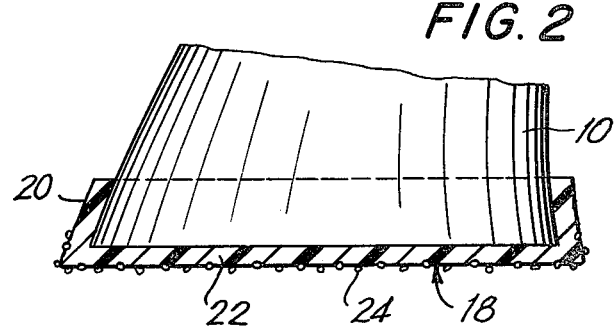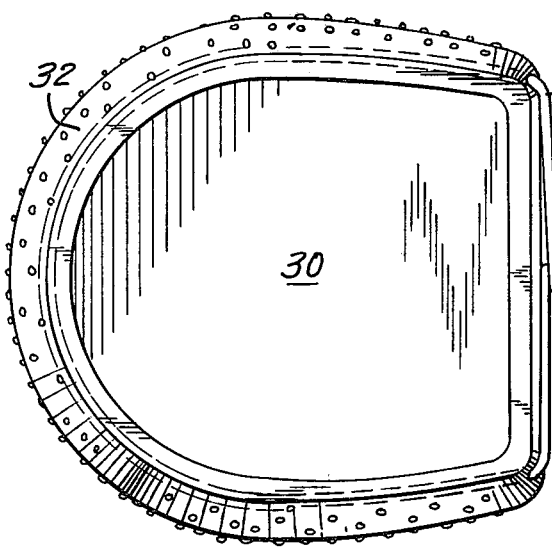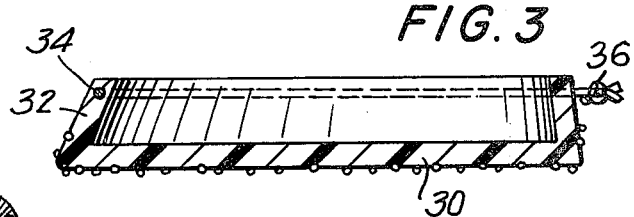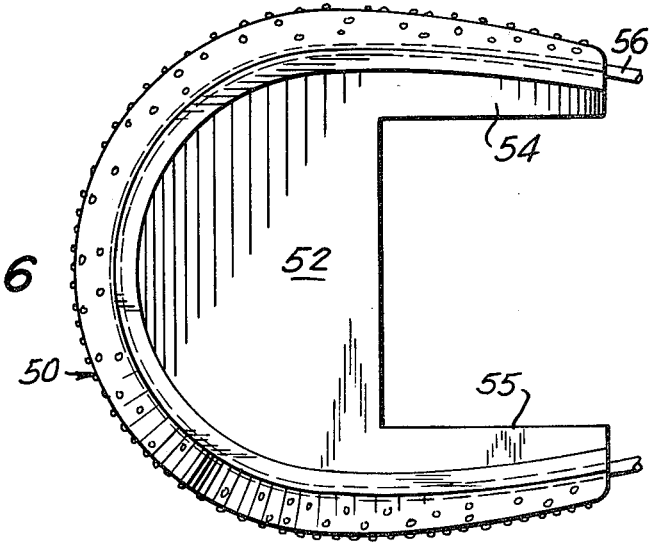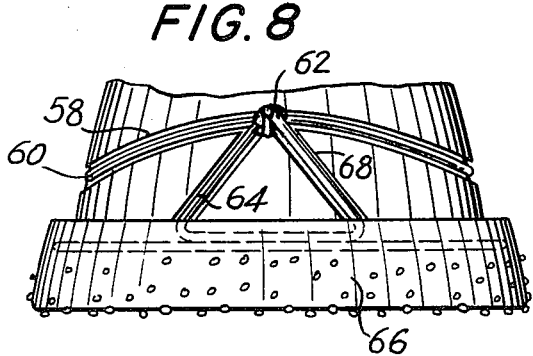

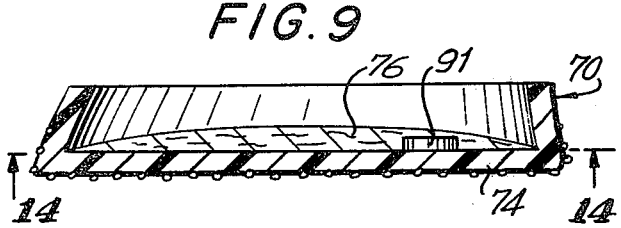
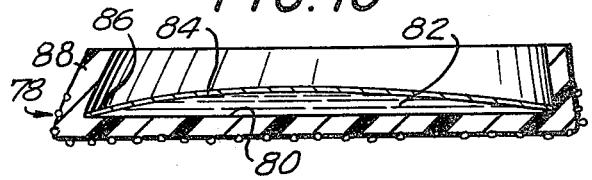
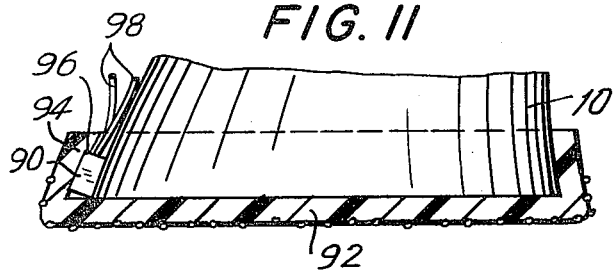
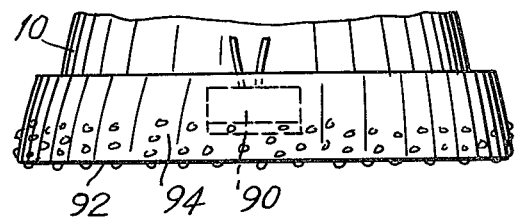
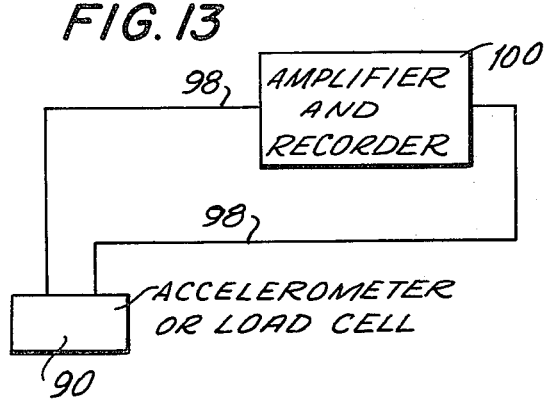
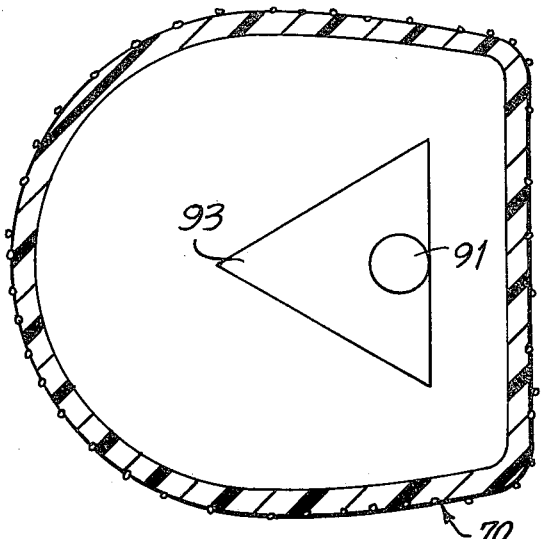
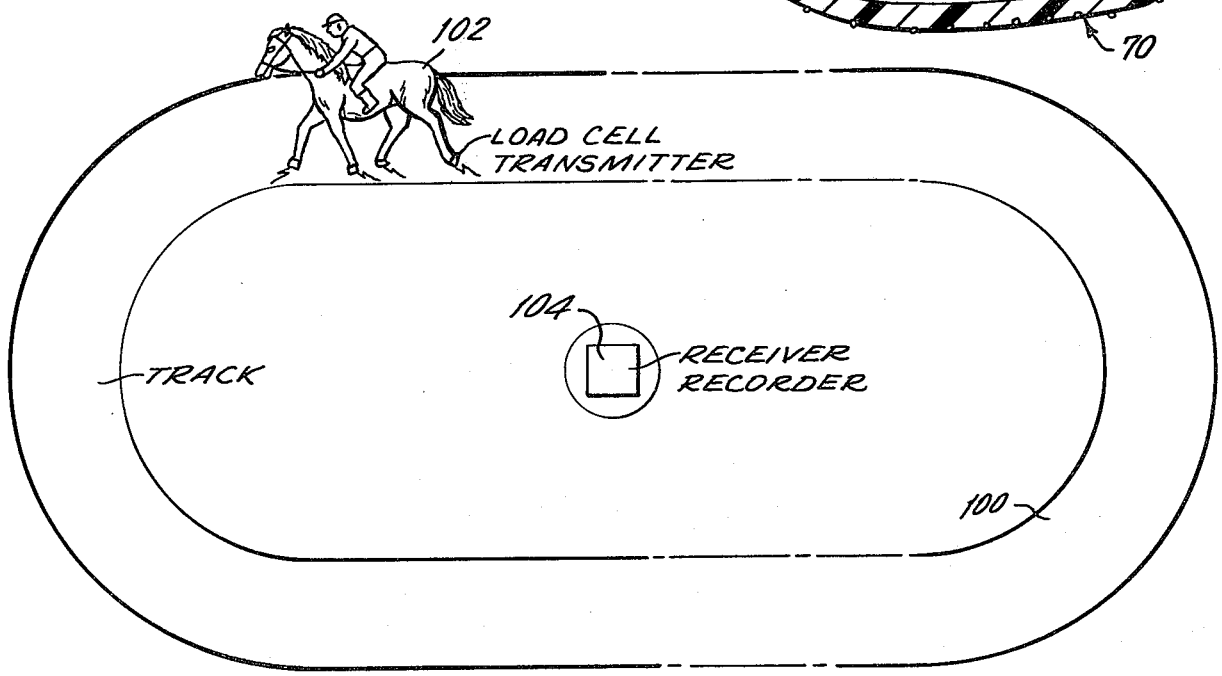

DEVICES RELATING TO HOOVES

BACKGROUND OF THE INVENTION

The present invention relates to devices pertaining to hooves of animals such as horses.

It is well known that conventional horseshoes suffer from serious drawbacks. Thus conventional horseshoes are in the form of metal bars nailed to the hoof, creating a number of problems both with respect to undesirable transmission of shock to the hoof as well as with respect to incapability of the conventional horseshoe to respond to the growth of the hoof and to deformation of the hoof during impact with the ground. The nails which are used conventially to fasten the shoe to the hoof create cracks and fissures in the hoof, and such cracks and fissures very often given rise to undesirable infection. Moreover, the precise behavior of the hoof during travelling of the animal, particularly the impact forces encountered by the hoof, are not known in detail.

Furthermore, when an animal such as a horse develops a fault, the detection of such a problem cannot at the present time be carried out at a stage of the development of the problem early enough to prevent serious measures from being taken.

SUMMARY OF THE INVENTION

It is accordingly a primary object of the present invention to provide devices relating to hooves, for alleviating the above problems.

In addition it is an object of the present invention to provide apparatus capable of deriving information with respect to the manner in which the hoof behaves during travel of the animal along the ground.

The device of the pesent invention includes the use of a sensing means, such as an accelerometer or load cell, which is attached to a hoof and provides signals to be picked up and recorded by suitable recording equipment simultaneously with the running of the animal, for example, so that signals resulting from engagement of hooves with the ground can be picked up and recorded.

BRIEF DESCRIPTION OF DRAWINGS

The invention is illustrated by way of example in the accompanying drawings which form part of this application and in which:

FIG. 1 is a schematic illustration of a shoeing method;

FIG. 2 is a schematic partly sectional elevation of a horseshoe;

FIG. 3 is a sectional elevation of a horseshoe provided with a fastening means;

FIG. 4 is a top plan view of the shoe of FIG. 3;

FIG. 5 is a sectional elevation of a further embodiment of a horseshoe;

FIGS. 6 and 7 are respectively plan and sectional elevations of yet another embodiment of a horseshoe;

FIG. 8 is a schematic fragmentary elevation showing further details of a fastening structure;

FIG. 9 shows a variation according to which medication or a load cell may be situated at the frog;

FIG. 10 shows a further variation according to which a load-distributing liquid may be situated at the frog;

FIGS. 11 and 12 are respectively a sectional elevation and front elevation schematically illustrating the manner in which an accelerometer may be attached to a hoof;

FIG. 13 illustrates schematically the manner in which the accelerometer is connected to further structure for recording the information provided by the accelerometer;

FIG. 14 is a schematic partly sectional view taken along line 14—14 of FIG. 9 in the direction of the arrows and showing in a schematic manner the relationship between a sensing means such as a load cell and the frog; and FIG. 15 is a schematic illustration of the manner in which signals can be transmitted so as to be picked up and recorded by suitable equipment.

DESCRIPTION OF PREFERRED EMBODIMENTS

Referring first to FIG. 1, it will be seen that there is applied to the hoof 10 of an animal such as a horse a liquid substance 12 which in the illustrated example is sprayed onto the hoof 10 as from a suitable spray can 14. The hoof 10 may initially be covered by a suitable masking material 16 which will prevent the liquid substance 12 from covering those parts of the hoof to which the shoe is not to be applied.

The liquid substance 12 is in the form of an elastomeric material which may, for example, be dissolved in a suitable solvent so that it can be sprayed under pressure from the container 14 in a well known manner, and when exposed to the other atmosphere the solvent will evaporate so as to leave a solidified elastomeric material at the hoof 10. If desired, the liquid substance may be situated in a suitable open container and with a suitable paint brush or the like the liquid substance may be painted directly onto the hoof.

It is to be understood that any elastomeric material capable of solidifying by a suitable chemical reaction can be utilized to form directly on a hoof a shoe of elastomeric material.

After this substance solidifies the masking material 16 is removed, and what remains is an elastomeric horseshoe which perfectly fits the hoof while being capable of yielding to impact forces and growing with the hoof. Because of the fact that the hoof tapers upwardly, the lip of the elastomeric shoe will engage the side surface of the hoof adjacent the sole thereof will retain the shoe on the hoof.

Thus, referring to FIG. 2 it will be seen that there is illustrated therein a horseshoe 18 which may be applied according to a method such as that shown in FIG. 1, this horseshoe 18 thus having a lower sheet of elastomeric material extending beneath the sole of the hoof while having an integral lip 20 which extends upwardly from and is integral with the periphery of the sheet 22 which extends beneath the sole of the hoof.

In order to prevent rapid wearing away of the elastomeric horseshoe 18, it has applied at least to its exterior surface a plurality of bodies 24 which are considerably harder than the elastomeric material of the horseshoe 18. These bodies 24 may take the form of particles of silicon carbide or tungsten carbide or they may take the form of flakes of sheet metal. These bodies 24 may be applied to the exterior surface of the elastomeric material 18 by dipping the latter into a container carrying the bodies 24 subsequent to application of the elastomeric material to the hoof but before the elastomeric material has completely solidified, so that in this way the particles 24 will become embedded in the elastomeric material and will adhere thereto upon solidification of the elastomeric material. However, it is also possible to distribute throughout the substance 12 while it is in liquid form the bodies 24 which thus become sprayed or otherwise applied with the liquid substance 12 directly onto the hoof 10, and in this way even better wear characteristics are provided since the hard bodies are distributed throughout the elastomeric material. In the case of dipping, before the elastomeric material solidifies it is simply placed against the bodies 24 while the latter are exposed in a suitable container, for example, so that through this simple expedient it is possible to provide the exterior surface of the elastomeric material 18 with a hard-wearing covering.

While the above shoe 18 will fit perfectly and be reliably retained by the hoof 10, nevertheless in order to enhance the security of the connection of the shoe 18 on the hoof 10, an arrangement such as shown in FIGS. 3 and 4 may be provided. Thus referring to FIGS. 3 and 4 it is seen that there is illustrated therein a horseshoe 30 which may be constructed in the same way as the shoe 18 except that the horseshoe 30 has embedded in the lip 32 thereof an elongated wire 34 which projects at the rear of the shoe 30, as is apparent from FIG. 4. This wire 34 may be pulled tightly and twisted, as shown at the free ends 36 of the wire 34, so as to provide in this way a perfectly secure connection of the horseshoe on the hoof.

As may be seen from FIG. 5, a horseshoe 38, which may also be identical with the horseshoe 18, is formed at its exterior surface, at the lip 40 thereof with a groove 42 which receives a fastening wire 44 which may be identical with the wire 34 and which may be pulled in the same way and twisted so as to increase the security of the connection of the shoe on the hoof.

In addition, as is shown in FIG. 5, it is possible to provide the shoe with vent openings 46 so that air can have access into and out of the interior of the shoe, making the shoe extremely comfortable to wear and remaining reliably on the hoof.

When shoes such as those shown in FIGS. 2–5 are prefabricated, the openings 46 can be preliminarily formed in the shoe, and of course the wire 34 or 44 can be embedded in the lip or situated in a groove thereof as described above. However, when the shoe is sprayed or painted on the hoof, as described above in connection with FIG. 1, then the wire 34 can be held around the hoof so as to become automatically embedded in the elastomeric material and suitable pins may be temporarily adhered or otherwise fixed to the exterior surface of the hoof where the bores or vent openings 46 are to be located, with these pins being pulled out after the material solidifies so as to leave the vent openings 46.

While in the above embodiments the horseshoe invariably has a lower sheet which covers the sole of the hoof, extending beneath the latter, it is not absolutely essential to completely cover the sole of the hoof. Thus FIGS. 6 and 7 show a embodiment of a horseshoe 50 which may be identical with the horseshoe of FIG. 3, except that the lower sheet 52 is of a substantially semicircular configuration and covers only the forward part of the sole, while peripheral portions 54 and 55 of the shoe extend rearwardly to the rear of the hoof with a wire such as a wire 56, identical with the wire 34, being provided to contribute to the security of the connection of the horseshoe 50 to the hoof.

In accordance with a further feature whch is illustrated in FIG. 8, the hoof 10 may be formed with grooves 58 to receive fastening wire such as the wire 60. This wire 60 may correspond to any of the wires 34, 44, or 56 referred to above, and the wire may include two portions one of which extends around the rear of the hoof and then to the front thereof along the grooves 58 to be twisted at the region 62, while a second wire 64 may extend upwardly from the front portion of the shoe 66, which corresponds to any of the above shoes, to proceed along the interior of additional grooves 68 for twisting together with the portions 62 as illustrated in FIG. 8. In this way an extremely secure connection is provided.

According to a further feature a horseshoe 70, which may correspond to any of the horseshoes described above, is provided at the inner surface 72 of the sheet 74 which extends beneath the sole of the hoof with a pad 76 of cotton wadding or the like. This pad may be impregnated with a suitable medication such as a suitable antiseptic or antibiotic material, so that in this way when required, medication may be maintained directly in engagement with the sole of the hoof.

Furthermore, as illustrated in FIG. 10, a horseshoe 78, which may also be identical with any of the above described horseshoes, has an inner surface 80 which forms part of a pocket 82. This pocket 82 is formed by the surface 80 and a sheet of stretchable elastic material 84 which is fused at its periphery 86 to the periphery of the surface 82 where it meets the lip 88. This fusion may be provided by a suitable solvent or the like. Thus between the surface 80 and the sheet 84 is formed a pocket 82, and this pocket 82 is filled in any suitable way with a liquid, as illustrated in FIG. 10. As a result a hydrostatic center support is provided for uniformly distributing the load to the frog. The liquid may be situated in the pocket 82 with a hypodermic needle or syringe, and the opening through which the liquid is introduced may then be closed in a suitable way or the lower sheet of the horseshoe 78 may be provided with a removable plug through which the liquid can be introduced.

Experience has shown that the exact behavior of the legs of an animal with respect to the ground during travel of the animal fluctuates with different leg conditions. Thus during an early stage of the development of a problem at a hoof, for example, the leg of the animal with such a problem will behave differently during running of the animal, for example, but the difference may be so minute at an early stage that it cannot readily be detected by watching the animal run, even if such observation is carried out by an extremely skilled experienced individual. In order to be able to detect such conditions at an extremely early stage, so as to be able to take measures to avoid further deterioration, in accordance with a further feature of apparatus according to the invention, there is provided a sensing means such as an accelerometer or load cell which is attached to the hoof. In a manner such as that illustrated in FIG. 11, an accelerometer 90 may be attached to the hoof. The accelerometer 90 is in itself a well known instrument which is capable of registering forces such as the impact force which will be encountered by the hoof 10 when engaging the ground, as when the animal runs along the ground. The horseshoe 92 serves in the illustrated example as a means for fastening the accelerometer 90 to the hoof 10. Thus, this horseshoe 92 may be made of an elastomeric material covered at its exterior surface with hard bodies such as the bodies 24, but in the embodiment of FIG. 11, as well as FIG. 12, the horseshoe 92 is formed at the front portion 94 of its lip with a recess 96 in which the accelerometer 90 is located so as to be maintained in this way at the hoof 10. For this purpose the horseshoe 92 may be applied, when still in the liquid form, around the accelerometer 90 which is maintained in any suitable way, such as by the suitable adhesive tape or the like, in engagement with the hoof 10 at the location illustrated. Where the horseshoe 92 is prefabricated, it is of course prefabricated with the recess 96 and then placed around the accelerometer 90, with the elastomeric material being sufficiently flexible particularly at the front region of the lip 94 to permit access to the recess 90 in order to introduce and remove the accelerometer 90 as required.

The accelerometer 90 is connected by suitable conductors 88 to an amplifier and recorder unit 100 which also is well known and which will serve to record the information provided by the accelerometer 90. Thus, the unit 100 will include a suitable recording instrument which may be automatically actuated through suitable electronic circuitry or the like, and the entire unit 100 may be mounted on the body of the animal, for example in the region of a saddle which is carried by the animal, with the wires 98 extending from the unit 100 to the accelerometer in the manner illustrated in FIG. 13 in a schematic manner.

While reference has been specifically made to an accelerometer above, as one embodiment of a sensing means of the invention, it is also possible to use for the sensing means a load cell such as the load cell 91 illustrated in FIGS. 9 and 14. This load cell 91 may be situated in the pad 76 of FIG. 9, instead of medication as referred to above. The load cell 91 is a well known instrument which responds to compression so as to provide a signal. For examle such well known load cells incorporate variable resistors which respond to distention of a diaphragm or the like so as to provide a resistance value corresponding to the compressive force acting on the load cell. As indicated in FIG. 14, it is preferred to locate the load cell 91 toward the rear hoof area, at the bottom thereof where the frog 93 is located, as designated schematically by the triangle in FIG. 14.

Thus, with such an arrangement it is possible to situate beneath each hoof a sensing means in the form of a load cell 91. This load cell 91 is combined with a well known miniature transmitter capable of transmitting radio waves of a predetermined frequency. Such miniature transmitters also are well known.

The manner in which such a construction is used is illustrated schematically in FIg. 15. Thus, FIG. 15 schematically illustrates a track 100 around which an animal 102 can travel, as shown schematically. FIG. 15 illustrates schematically how the several hooves of the animal are provided with the load cell-transmitter units which will transmit signals at a suitable frequency to be picked up by a receiver and recorder unit 104 which may be situated at the center of the track, as illustrated in FIG. 15. The frequencies at which the four signals are transmitted from the four hoofs may be different and four separate pickups may be provided with the recordings being made on four distinct channels of a recording tape, for example, so that thereafter the tape may be played back and the sound produced can at a suitable oscilloscope, for example, create certain waves which can be photographed and recorded.

Thus, through the expedients illustrated in FIGS. 11–15 it is possible to obtain information with respect to the behavior of the hoof 10 during travel of the animal along the ground, so that in this way with this information it is possible to design a horseshoe in a manner which will achieve the best possible comfort for the animal and detect incipient faults. Of course, the invention is illustrated in FIGS. 11–13 only with respect to a single hoof, but it is to be understood that a number of accelerometers 90 may be respectively situated at two or more of the hooves of the animal, with wires from the accelerometers being connected to one or more of the units 100 for recording the behavior of the accelerometers.

Of course, where several accelerometers and wires are extended from the several hooves of an animal to a recording unit at the saddle, a considerable inconvenience results because of the necessity of mounting such a unit directly on the animal with the wires extending upwardly to the unit at the saddle. Such a unit may also be a suitable tape recorder having four distinct channels to receive four distinct recordings from the different hooves, and of course these recordings can be identified with respect to the particular hooves, in the same way as the signals provided in the manner shown in FIG. 15 and described above. Of course the arrangement shown in FIG. 15 is far more preferable since the inconvenience of wires and mounting a unit directly on the animal is avoided. Thus accelerometers also may be associated with suitable miniaturized transmitters for sending signals to a receiving and recording unit as indicated in FIG. 15.

Thus, with these arrangements as shown in FIGS. 11–15, it is possible to keep a record in connection with a particular animal. For example once each month a procedure is carried out according to which signals in connection with a particular animal are recorded, and each time a set of signals are provided for the separate hooves of a given animal, these signals may be compared with previously recorded signals as from the previous month or months. By such a comparison of the recorded signals it is possible to detect at an extremely early stage whether there is a variation in the performance of a particular animal which should be looked into further. For example it may well happen that the signal emanating from one hoof illustrates that the animal has a tendency, which may be extremely slight, to favor this particular hoof, so that as a result it is possible to check into the condition of the animal at an extremely early stage before serious problems arise.

It will thus be seen that with th above-described features of the invention the problems involved with conventional horseshoes are alleviated and in addition it is possible to achieve information with respect to the behavior of the hooves of the animal, with this information being suitable for use in the designing of horseshoes, for example.

The material sprayed or painted to form an elastomeric shoe directly on the hoof can be a suitable epoxy or RTV (room temperature vulcanizing material).

For accelerometer 90, a Columbia Model 606-3 accelerometer is suitable. An SR4 strain gauge load cell bonded to a capsule is suitable for load cell 91 and is utilized with a suitable miniature transmitter. The recordings were all made on a modified Sony recorder.

What is claimed is:

1. In a device for providing information with respect to the behavior of a hoof, sensing means for sensing the manner in which a hoof behaves during use of the hoof by an animal and for providing signals corresponding to the behavior of the hoof, mounting means operatively connected with said sensing means for mounting the latter on a hoof, and means for receiving and recording said signals provided by said sensing means, said mounting means including a horseshoe which holds the sensing means at the hoof.

2. The combination of claim 1 and wherein the sensing means is an accelerometer.

3. The combination of claim 1 and wherein the sensing means is a load cell.

4. The combination of claim 2 and wherein the horseshoe is made of an elastomeric material and is formed adjacent a side surface of the hoof with a recess in which the accelerometer is located.

5. The combination of claim 3 and wherein the horseshoe accommodates the load cell toward the rear of the bottom surface of a hoof at the frog thereof.

6. The combination of claim 5 and wherein a pad is carried by the horseshoe between the latter and the hoof and surrounds the load cell.

* * * * *